United States Patent
Srinivasan et al.

(10) Patent No.: US 7,833,779 B2
(45) Date of Patent: Nov. 16, 2010

(54) METHODS AND SYSTEMS FOR POLYNUCLEOTIDE DETECTION

(75) Inventors: Subha Srinivasan, Greenbrae, CA (US); Jonathan Bingham, San Francisco, CA (US)

(73) Assignee: Jivan Biologies Inc., Larkspur, CA (US)

( * ) Notice: Subject to any disclaimer, the term of this patent is extended or adjusted under 35 U.S.C. 154(b) by 1274 days.

(21) Appl. No.: 10/272,461

(22) Filed: Oct. 16, 2002

(65) Prior Publication Data

US 2004/0076959 A1    Apr. 22, 2004

Related U.S. Application Data

(63) Continuation-in-part of application No. 10/146,720, filed on May 14, 2002, now Pat. No. 7,340,349.

(60) Provisional application No. 60/307,911, filed on Jul. 25, 2001, provisional application No. 60/343,298, filed on Dec. 21, 2001, provisional application No. 60/329,914, filed on Oct. 17, 2001.

(51) Int. Cl.
   - C12M 1/34 (2006.01)
   - C12M 3/00 (2006.01)
   - C07H 21/02 (2006.01)
   - C07H 21/04 (2006.01)
   - C12Q 1/68 (2006.01)

(52) U.S. Cl. ............. 435/287.2; 435/6; 536/23.1; 536/24.3

(58) Field of Classification Search .......... None
See application file for complete search history.

(56) References Cited

U.S. PATENT DOCUMENTS

| | | | |
|---|---|---|---|
| 5,057,410 A * | 10/1991 | Kawasaki et al. | 435/6 |
| 6,001,567 A * | 12/1999 | Brow et al. | 435/6 |
| 6,007,231 A | 12/1999 | Vijg et al. | |
| 6,100,030 A * | 8/2000 | McCasky Feazel et al. | 435/6 |
| 6,171,793 B1 | 1/2001 | Phillips et al. | |
| 6,210,892 B1 | 4/2001 | Bennett et al. | |
| 6,303,301 B1 | 10/2001 | Mack | |
| 6,632,610 B2 * | 10/2003 | Thill | 435/6 |
| 6,713,257 B2 | 3/2004 | Shoemaker et al. | |
| 6,881,571 B1 * | 4/2005 | Schweighoffer et al. | 435/287.2 |
| 6,887,662 B1 * | 5/2005 | Alajem et al. | 435/6 |
| 2002/0048763 A1 | 4/2002 | Penn et al. | |
| 2002/0081590 A1 | 6/2002 | Penn et al. | |
| 2003/0040870 A1 * | 2/2003 | Anderson et al. | 702/20 |
| 2003/0097223 A1 | 5/2003 | Nakae et al. | |
| 2003/0219805 A1 * | 11/2003 | Kelman et al. | 435/6 |
| 2005/0214824 A1 * | 9/2005 | Balaban | 435/6 |
| 2006/0199208 A1 | 9/2006 | Srinivasan et al. | |

FOREIGN PATENT DOCUMENTS

| | | | | |
|---|---|---|---|---|
| EP | 0 668 350 A1 | | 8/1995 | |
| WO | WO 99/46403 | * | 9/1999 | 435/6 |
| WO | WO 00/47765 | * | 8/2000 | |
| WO | WO 01/81632 A1 | | 11/2001 | |
| WO | WO 02/16650 A2 | | 2/2002 | |
| WO | WO 02/068579 A2 | | 9/2002 | |

OTHER PUBLICATIONS

Williams et al; Analytical Biochemistry, vol. 271, pp. 194-197, 1999.*
Virts et al; Molecular Immunology, vol. 35, pp. 167-176, 1998.*
Adams, M.D., et al., *Science*, 252:1651-1656, (1991).
Black, D.L., *Cell*, 103:367-370, (2000).
Brown, P.O. and Botstein, D., *Nature Genetics Supplement*, 21:33-37, (1999).
Burge, C. and Karlin, S., *J. Mol. Biol.*, 268(1):78-94, (1997).
Hanke, J., et al., *Trends in Genetics*, 15(10):389-390, (1999).
Hu, G.K., et al., *Genome Research*, 11:1237-1245, (2001).
Lander, E.S., et al., *Nature*, 409:860-921, (2001).
Lin et al., *Neuron*, 18:153-166 (1997).
Maas et al., *Clinical Cancer Research*, 7:868-875 (2001).
Rozen et al., Bioinformatics: Methods and Protocols: (Misener and Krawetz EDS. Methods in Biology vol. 132, Humana Press, Totowa, NJ, Chapter 20, p. 365-386) (2000).
Shoemaker, D.D., et al., *Nature*, 409:922-926, (2001).
Singh, Gautam B., Bioinformatics: Methods and Protocols:(Misener and Krawetz EDS. Methods in Molecular Biology vol. 132, Humana Press, Totowa, NJ, Chapter 19, p. 351-364) (2000).
Sorek, R. and Amitai, M., *Nature Biotechnology*, 19:196, (2001).
Svineng et al., *Biochemical Journal*, 330:1255-1263 (1998).
Virts et al., *Molecular Immunology*, 35:167-176 (1998).
Williams et al., *Analytical Biochemistry*, 271:194-197 (1999).
Kan, Z., et al., *Genome Research*, 11:889-900, (2001).

* cited by examiner

*Primary Examiner*—Jehanne S Sitton

(57) ABSTRACT

Optimization techniques for selecting indicator polynucleotides for an experiment and for determining expression levels resulting from the experiment. The optimization technique corrects for variations in polynucleotide melting temperatures during analysis of the experimental results. The optimization technique selects set of indicator polynucleotides for the experiment. The optimization technique then performs the experiment with the indicator polynucleotides and a sample and identifies the relative amounts of the indicated polynucleotides. The optimization technique then adjusts the relative amounts of the indicated polynucleotides based on melting temperatures associated with the indicator polynucleotides.

1 Claim, 3 Drawing Sheets

SEQUENCE LISTING

<160> NUMBER OF SEQ ID NOS: 104

<210> SEQ ID NO 1
<211> LENGTH: 20
<212> TYPE: DNA
<213> ORGANISM: Homo sapiens

<400> SEQUENCE: 1
cgcgcccagg gatcctccag					20

<210> SEQ ID NO 2
<211> LENGTH: 20
<212> TYPE: DNA
<213> ORGANISM: Homo sapiens

<400> SEQUENCE: 2
gcgcagatcg atttgaatat					20

<210> SEQ ID NO 3
<211> LENGTH: 20
<212> TYPE: DNA
<213> ORGANISM: Homo sapiens

<400> SEQUENCE: 3
ggaggccgct gacctctgca					20

<210> SEQ ID NO 4
<211> LENGTH: 20
<212> TYPE: DNA
<213> ORGANISM: Homo sapiens

<400> SEQUENCE: 4
agacctgcag gtatgggttc					20

<210> SEQ ID NO 5
<211> LENGTH: 20
<212> TYPE: DNA
<213> ORGANISM: Homo sapiens

<400> SEQUENCE: 5
tgcagcaaac aacacagggg					20

<210> SEQ ID NO 6
<211> LENGTH: 20
<212> TYPE: DNA
<213> ORGANISM: Homo sapiens

<400> SEQUENCE: 6
aatgcttcag ctccacctga					20

<210> SEQ ID NO 7
<211> LENGTH: 20
<212> TYPE: DNA

<213> ORGANISM: Homo sapiens

<400> SEQUENCE: 7
agtcacagac ctgcccaatg                                        20

<210> SEQ ID NO 8
<211> LENGTH: 20
<212> TYPE: DNA
<213> ORGANISM: Homo sapiens

<400> SEQUENCE: 8
attaccataa ctattgttaa                                        20

<210> SEQ ID NO 9
<211> LENGTH: 20
<212> TYPE: DNA
<213> ORGANISM: Homo sapiens

<400> SEQUENCE: 9
gctcctccag tgaaaggagc                                        20

<210> SEQ ID NO 10
<211> LENGTH: 20
<212> TYPE: DNA
<213> ORGANISM: Homo sapiens

<400> SEQUENCE: 10
cctgctacca ctttgatgag                                        20

<210> SEQ ID NO 11
<211> LENGTH: 20
<212> TYPE: DNA
<213> ORGANISM: Homo sapiens

<400> SEQUENCE: 11
cctgggattg gttttcatgg                                        20

<210> SEQ ID NO 12
<211> LENGTH: 20
<212> TYPE: DNA
<213> ORGANISM: Homo sapiens

<400> SEQUENCE: 12
caaatggctg gtacgtcttc                                        20

<210> SEQ ID NO 13
<211> LENGTH: 20
<212> TYPE: DNA
<213> ORGANISM: Homo sapiens

<400> SEQUENCE: 13
gatgaaagag acagacacct                                        20

<210> SEQ ID NO 14
<211> LENGTH: 20
<212> TYPE: DNA
<213> ORGANISM: Homo sapiens

<400> SEQUENCE: 14
tccagcacca tttcaaccac                                        20

<210> SEQ ID NO 15
<211> LENGTH: 20

<212> TYPE: DNA
<213> ORGANISM: Homo sapiens

<400> SEQUENCE: 15
tggacccagt ggaacccaag                                                    20

<210> SEQ ID NO 16
<211> LENGTH: 20
<212> TYPE: DNA
<213> ORGANISM: Homo sapiens

<400> SEQUENCE: 16
aggatgactg atgtagacag                                                    20

<210> SEQ ID NO 17
<211> LENGTH: 20
<212> TYPE: DNA
<213> ORGANISM: Homo sapiens

<400> SEQUENCE: 17
aagcacaccc tcccctcatt                                                    20

<210> SEQ ID NO 18
<211> LENGTH: 20
<212> TYPE: DNA
<213> ORGANISM: Homo sapiens

<400> SEQUENCE: 18
acaagcacaa tccaggcaac                                                    20

<210> SEQ ID NO 19
<211> LENGTH: 20
<212> TYPE: DNA
<213> ORGANISM: Homo sapiens

<400> SEQUENCE: 19
ggtttggcaa cagatggcat                                                    20

<210> SEQ ID NO 20
<211> LENGTH: 20
<212> TYPE: DNA
<213> ORGANISM: Homo sapiens

<400> SEQUENCE: 20
gggacagctg cagcctcagc                                                    20

<210> SEQ ID NO 21
<211> LENGTH: 20
<212> TYPE: DNA
<213> ORGANISM: Homo sapiens

<400> SEQUENCE: 21
gacagttcct ggactgattt                                                    20

<210> SEQ ID NO 22
<211> LENGTH: 20
<212> TYPE: DNA
<213> ORGANISM: Homo sapiens

<400> SEQUENCE: 22
agaaggatgg atatggactc                                                    20

<210> SEQ ID NO 23

```
<211> LENGTH: 20
<212> TYPE: DNA
<213> ORGANISM: Homo sapiens

<400> SEQUENCE: 23
aatccaaaca caggtttggt                                              20

<210> SEQ ID NO 24
<211> LENGTH: 20
<212> TYPE: DNA
<213> ORGANISM: Homo sapiens

<400> SEQUENCE: 24
atgacaacgc agcagagtaa                                              20

<210> SEQ ID NO 25
<211> LENGTH: 20
<212> TYPE: DNA
<213> ORGANISM: Homo sapiens

<400> SEQUENCE: 25
gaaggcttgg aagaagataa                                              20

<210> SEQ ID NO 26
<211> LENGTH: 20
<212> TYPE: DNA
<213> ORGANISM: Homo sapiens

<400> SEQUENCE: 26
acatcaagca ataggaatga                                              20

<210> SEQ ID NO 27
<211> LENGTH: 20
<212> TYPE: DNA
<213> ORGANISM: Homo sapiens

<400> SEQUENCE: 27
acgaaggaaa gcaggacctt                                              20

<210> SEQ ID NO 28
<211> LENGTH: 20
<212> TYPE: DNA
<213> ORGANISM: Homo sapiens

<400> SEQUENCE: 28
tccttatcag gagaccaaga                                              20

<210> SEQ ID NO 29
<211> LENGTH: 20
<212> TYPE: DNA
<213> ORGANISM: Homo sapiens

<400> SEQUENCE: 29
cagtgggggg tcccatacca                                              20

<210> SEQ ID NO 30
<211> LENGTH: 20
<212> TYPE: DNA
<213> ORGANISM: Homo sapiens

<400> SEQUENCE: 30
gaatcagatg gacactcaca                                              20
```

```
<210> SEQ ID NO 31
<211> LENGTH: 20
<212> TYPE: DNA
<213> ORGANISM: Homo sapiens

<400> SEQUENCE: 31
ggagcaaaca caacctctgg                                                      20

<210> SEQ ID NO 32
<211> LENGTH: 20
<212> TYPE: DNA
<213> ORGANISM: Homo sapiens

<400> SEQUENCE: 32
caaattccag aatggctgat                                                      20

<210> SEQ ID NO 33
<211> LENGTH: 20
<212> TYPE: DNA
<213> ORGANISM: Homo sapiens

<400> SEQUENCE: 33
ccttggcttt gattcttgca                                                      20

<210> SEQ ID NO 34
<211> LENGTH: 20
<212> TYPE: DNA
<213> ORGANISM: Homo sapiens

<400> SEQUENCE: 34
gtcgaagaag gtgtgggcag                                                      20

<210> SEQ ID NO 35
<211> LENGTH: 20
<212> TYPE: DNA
<213> ORGANISM: Homo sapiens

<400> SEQUENCE: 35
tcgttccagt tcccacttgg                                                      20

<210> SEQ ID NO 36
<211> LENGTH: 16
<212> TYPE: DNA
<213> ORGANISM: Homo sapiens

<400> SEQUENCE: 36
gcccagggat cctcca                                                          16

<210> SEQ ID NO 37
<211> LENGTH: 24
<212> TYPE: DNA
<213> ORGANISM: Homo sapiens

<400> SEQUENCE: 37
cgcagatcga tttgaatata acct                                                 24

<210> SEQ ID NO 38
<211> LENGTH: 16
<212> TYPE: DNA
<213> ORGANISM: Homo sapiens

<400> SEQUENCE: 38
aggccgctga cctctg                                                          16
```

```
<210> SEQ ID NO 39
<211> LENGTH: 19
<212> TYPE: DNA
<213> ORGANISM: Homo sapiens

<400> SEQUENCE: 39
gacctgcagg tatgggttc                                                19

<210> SEQ ID NO 40
<211> LENGTH: 19
<212> TYPE: DNA
<213> ORGANISM: Homo sapiens

<400> SEQUENCE: 40
tgcagcaaac aacacaggg                                                19

<210> SEQ ID NO 41
<211> LENGTH: 19
<212> TYPE: DNA
<213> ORGANISM: Homo sapiens

<400> SEQUENCE: 41
aatgcttcag ctccacctg                                                19

<210> SEQ ID NO 42
<211> LENGTH: 19
<212> TYPE: DNA
<213> ORGANISM: Homo sapiens

<400> SEQUENCE: 42
agtcacagac ctgcccaat                                                19

<210> SEQ ID NO 43
<211> LENGTH: 26
<212> TYPE: DNA
<213> ORGANISM: Homo sapiens

<400> SEQUENCE: 43
caattaccat aactattgtt aaccgt                                        26

<210> SEQ ID NO 44
<211> LENGTH: 19
<212> TYPE: DNA
<213> ORGANISM: Homo sapiens

<400> SEQUENCE: 44
ctcctccagt gaaaggagc                                                19

<210> SEQ ID NO 45
<211> LENGTH: 20
<212> TYPE: DNA
<213> ORGANISM: Homo sapiens

<400> SEQUENCE: 45
cctgctacca ctttgatgag                                               20

<210> SEQ ID NO 46
<211> LENGTH: 22
<212> TYPE: DNA
<213> ORGANISM: Homo sapiens

<400> SEQUENCE: 46
cctgggattg gttttcatgg tt                                            22
```

```
<210> SEQ ID NO 47
<211> LENGTH: 20
<212> TYPE: DNA
<213> ORGANISM: Homo sapiens

<400> SEQUENCE: 47
caaatggctg gtacgtcttc                                              20

<210> SEQ ID NO 48
<211> LENGTH: 22
<212> TYPE: DNA
<213> ORGANISM: Homo sapiens

<400> SEQUENCE: 48
aagatgaaag agacagacac ct                                           22

<210> SEQ ID NO 49
<211> LENGTH: 20
<212> TYPE: DNA
<213> ORGANISM: Homo sapiens

<400> SEQUENCE: 49
ccagcaccat ttcaaccaca                                              20

<210> SEQ ID NO 50
<211> LENGTH: 18
<212> TYPE: DNA
<213> ORGANISM: Homo sapiens

<400> SEQUENCE: 50
ggacccagtg gaacccaa                                                18

<210> SEQ ID NO 51
<211> LENGTH: 23
<212> TYPE: DNA
<213> ORGANISM: Homo sapiens

<400> SEQUENCE: 51
aaggatgact gatgtagaca gaa                                          23

<210> SEQ ID NO 52
<211> LENGTH: 17
<212> TYPE: DNA
<213> ORGANISM: Homo sapiens

<400> SEQUENCE: 52
gcacaccctc ccctcat                                                 17

<210> SEQ ID NO 53
<211> LENGTH: 21
<212> TYPE: DNA
<213> ORGANISM: Homo sapiens

<400> SEQUENCE: 53
tacaagcaca atccaggcaa c                                            21

<210> SEQ ID NO 54
<211> LENGTH: 20
<212> TYPE: DNA
<213> ORGANISM: Homo sapiens

<400> SEQUENCE: 54
```

```
ggtttggcaa cagatggcat                                              20
```

<210> SEQ ID NO 55
<211> LENGTH: 17
<212> TYPE: DNA
<213> ORGANISM: Homo sapiens

<400> SEQUENCE: 55

```
ggacagctgc agcctca                                                 17
```

<210> SEQ ID NO 56
<211> LENGTH: 21
<212> TYPE: DNA
<213> ORGANISM: Homo sapiens

<400> SEQUENCE: 56

```
gacagttcct ggactgattt c                                            21
```

<210> SEQ ID NO 57
<211> LENGTH: 22
<212> TYPE: DNA
<213> ORGANISM: Homo sapiens

<400> SEQUENCE: 57

```
aagaaggatg gatatggact cc                                           22
```

<210> SEQ ID NO 58
<211> LENGTH: 22
<212> TYPE: DNA
<213> ORGANISM: Homo sapiens

<400> SEQUENCE: 58

```
caaatccaaa cacaggtttg gt                                           22
```

<210> SEQ ID NO 59
<211> LENGTH: 23
<212> TYPE: DNA
<213> ORGANISM: Homo sapiens

<400> SEQUENCE: 59

```
aatgacaacg cagcagagta att                                          23
```

<210> SEQ ID NO 60
<211> LENGTH: 23
<212> TYPE: DNA
<213> ORGANISM: Homo sapiens

<400> SEQUENCE: 60

```
gaaggcttgg aagaagataa aga                                          23
```

<210> SEQ ID NO 61
<211> LENGTH: 23
<212> TYPE: DNA
<213> ORGANISM: Homo sapiens

<400> SEQUENCE: 61

```
gacatcaagc aataggaatg atg                                          23
```

<210> SEQ ID NO 62
<211> LENGTH: 19
<212> TYPE: DNA
<213> ORGANISM: Homo sapiens

<400> SEQUENCE: 62

-continued acgaaggaaa gcaggacct                                                    19

<210> SEQ ID NO 63
<211> LENGTH: 21
<212> TYPE: DNA
<213> ORGANISM: Homo sapiens

<400> SEQUENCE: 63
ttccttatca ggagaccaag a                                                 21

<210> SEQ ID NO 64
<211> LENGTH: 16
<212> TYPE: DNA
<213> ORGANISM: Homo sapiens

<400> SEQUENCE: 64 tgggggtcc catacc                                                        16

<210> SEQ ID NO 65
<211> LENGTH: 22
<212> TYPE: DNA
<213> ORGANISM: Homo sapiens

<400> SEQUENCE: 65
tgaatcagat ggacactcac at                                                22

<210> SEQ ID NO 66
<211> LENGTH: 19
<212> TYPE: DNA
<213> ORGANISM: Homo sapiens

<400> SEQUENCE: 66
ggagcaaaca caacctctg                                                    19

<210> SEQ ID NO 67
<211> LENGTH: 22
<212> TYPE: DNA
<213> ORGANISM: Homo sapiens

<400> SEQUENCE: 67
ccaaattcca gaatggctga tc                                                22

<210> SEQ ID NO 68
<211> LENGTH: 21
<212> TYPE: DNA
<213> ORGANISM: Homo sapiens

<400> SEQUENCE: 68
ccttggcttt gattcttgca g                                                 21

<210> SEQ ID NO 69
<211> LENGTH: 18
<212> TYPE: DNA
<213> ORGANISM: Homo sapiens

<400> SEQUENCE: 69
gtcgaagaag gtgtgggc                                                     18

<210> SEQ ID NO 70
<211> LENGTH: 19
<212> TYPE: DNA
<213> ORGANISM: Homo sapiens

```
<400> SEQUENCE: 70
tcgttccagt tcccacttg                                          19

<210> SEQ ID NO 71
<211> LENGTH: 30
<212> TYPE: DNA
<213> ORGANISM: Homo sapiens

<400> SEQUENCE: 71
gcctggcgca gatcgatttg aatataacct                              30

<210> SEQ ID NO 72
<211> LENGTH: 30
<212> TYPE: DNA
<213> ORGANISM: Homo sapiens

<400> SEQUENCE: 72
atttgagacc tgcaggtatg ggttcataga                              30

<210> SEQ ID NO 73
<211> LENGTH: 30
<212> TYPE: DNA
<213> ORGANISM: Homo sapiens

<400> SEQUENCE: 73
gcttcaatgc ttcagctcca cctgaagaag                              30

<210> SEQ ID NO 74
<211> LENGTH: 30
<212> TYPE: DNA
<213> ORGANISM: Homo sapiens

<400> SEQUENCE: 74
gaccaattac cataactatt gttaaccgtg                              30

<210> SEQ ID NO 75
<211> LENGTH: 30
<212> TYPE: DNA
<213> ORGANISM: Homo sapiens

<400> SEQUENCE: 75
gaatccctgc taccactttg atgagcacta                              30

<210> SEQ ID NO 76
<211> LENGTH: 30
<212> TYPE: DNA
<213> ORGANISM: Homo sapiens

<400> SEQUENCE: 76
caacacaaat ggctggtacg tcttcaaata                              30

<210> SEQ ID NO 77
<211> LENGTH: 30
<212> TYPE: DNA
<213> ORGANISM: Homo sapiens

<400> SEQUENCE: 77
ttatctccag caccatttca accacaccac                              30

<210> SEQ ID NO 78
<211> LENGTH: 30
<212> TYPE: DNA
<213> ORGANISM: Homo sapiens
```

-continued

<400> SEQUENCE: 78
ccacaaggat gactgatgta gacagaaatg                                        30

<210> SEQ ID NO 79
<211> LENGTH: 30
<212> TYPE: DNA
<213> ORGANISM: Homo sapiens

<400> SEQUENCE: 79
attctacaag cacaatccag gcaactccta                                        30

<210> SEQ ID NO 80
<211> LENGTH: 30
<212> TYPE: DNA
<213> ORGANISM: Homo sapiens

<400> SEQUENCE: 80
caacagggac agctgcagcc tcagctcata                                        30

<210> SEQ ID NO 81
<211> LENGTH: 30
<212> TYPE: DNA
<213> ORGANISM: Homo sapiens

<400> SEQUENCE: 81
caggaagaag gatggatatg gactccagtc                                        30

<210> SEQ ID NO 82
<211> LENGTH: 30
<212> TYPE: DNA
<213> ORGANISM: Homo sapiens

<400> SEQUENCE: 82
tttcaatgac aacgcagcag agtaattctc                                        30

<210> SEQ ID NO 83
<211> LENGTH: 30
<212> TYPE: DNA
<213> ORGANISM: Homo sapiens

<400> SEQUENCE: 83
ctctgacatc aagcaatagg aatgatgtca                                        30

<210> SEQ ID NO 84
<211> LENGTH: 30
<212> TYPE: DNA
<213> ORGANISM: Homo sapiens

<400> SEQUENCE: 84
atcgttcctt atcaggagac caagacacat                                        30

<210> SEQ ID NO 85
<211> LENGTH: 30
<212> TYPE: DNA
<213> ORGANISM: Homo sapiens

<400> SEQUENCE: 85
gatctgaatc agatggacac tcacatggga                                        30

<210> SEQ ID NO 86
<211> LENGTH: 30
<212> TYPE: DNA

<213> ORGANISM: Homo sapiens

<400> SEQUENCE: 86
caccccaaat tccagaatgg ctgatcatct         30

<210> SEQ ID NO 87
<211> LENGTH: 30
<212> TYPE: DNA
<213> ORGANISM: Homo sapiens

<400> SEQUENCE: 87
caacagtcga agaaggtgtg ggcagaagaa         30

<210> SEQ ID NO 88
<211> LENGTH: 28
<212> TYPE: DNA
<213> ORGANISM: Homo sapiens

<400> SEQUENCE: 88
ggcgcagatc gatttgaata taacctgc         28

<210> SEQ ID NO 89
<211> LENGTH: 28
<212> TYPE: DNA
<213> ORGANISM: Homo sapiens

<400> SEQUENCE: 89
tgagacctgc aggtatgggt tcatagaa         28

<210> SEQ ID NO 90
<211> LENGTH: 27
<212> TYPE: DNA
<213> ORGANISM: Homo sapiens

<400> SEQUENCE: 90
gcttcaatgc ttcagctcca cctgaag         27

<210> SEQ ID NO 91
<211> LENGTH: 34
<212> TYPE: DNA
<213> ORGANISM: Homo sapiens

<400> SEQUENCE: 91
tggaccaatt accataacta ttgttaaccg tgat         34

<210> SEQ ID NO 92
<211> LENGTH: 27
<212> TYPE: DNA
<213> ORGANISM: Homo sapiens

<400> SEQUENCE: 92
aatccctgct accactttga tgagcac         27

<210> SEQ ID NO 93
<211> LENGTH: 31
<212> TYPE: DNA
<213> ORGANISM: Homo sapiens

<400> SEQUENCE: 93
caacacaaat ggctggtacg tcttcaaata c         31

<210> SEQ ID NO 94
<211> LENGTH: 27

```
<212> TYPE: DNA
<213> ORGANISM: Homo sapiens

<400> SEQUENCE: 94
tatctccagc accatttcaa ccacacc                                        27

<210> SEQ ID NO 95
<211> LENGTH: 30
<212> TYPE: DNA
<213> ORGANISM: Homo sapiens

<400> SEQUENCE: 95
cacaaggatg actgatgtag acagaaatgg                                     30

<210> SEQ ID NO 96
<211> LENGTH: 28
<212> TYPE: DNA
<213> ORGANISM: Homo sapiens

<400> SEQUENCE: 96
cattctacaa gcacaatcca ggcaactc                                       28

<210> SEQ ID NO 97
<211> LENGTH: 20
<212> TYPE: DNA
<213> ORGANISM: Homo sapiens

<400> SEQUENCE: 97
gggacagctg cagcctcagc                                                20

<210> SEQ ID NO 98
<211> LENGTH: 27
<212> TYPE: DNA
<213> ORGANISM: Homo sapiens

<400> SEQUENCE: 98
aggaagaagg atggatatgg actccag                                        27

<210> SEQ ID NO 99
<211> LENGTH: 30
<212> TYPE: DNA
<213> ORGANISM: Homo sapiens

<400> SEQUENCE: 99
tttcaatgac aacgcagcag agtaattctc                                     30

<210> SEQ ID NO 100
<211> LENGTH: 32
<212> TYPE: DNA
<213> ORGANISM: Homo sapiens

<400> SEQUENCE: 100
ctctgacatc aagcaatagg aatgatgtca ca                                  32

<210> SEQ ID NO 101
<211> LENGTH: 27
<212> TYPE: DNA
<213> ORGANISM: Homo sapiens

<400> SEQUENCE: 101
cgttccttat caggagacca agacaca                                        27

<210> SEQ ID NO 102
```

```
<211> LENGTH: 29
<212> TYPE: DNA
<213> ORGANISM: Homo sapiens

<400> SEQUENCE: 102
ggatctgaat cagatggaca ctcacatgg                                    29

<210> SEQ ID NO 103
<211> LENGTH: 29
<212> TYPE: DNA
<213> ORGANISM: Homo sapiens

<400> SEQUENCE: 103
accccaaatt ccagaatggc tgatcatct                                    29

<210> SEQ ID NO 104
<211> LENGTH: 25
<212> TYPE: DNA
<213> ORGANISM: Homo sapiens

<400> SEQUENCE: 104
acagtcgaag aaggtgtggg cagaa                                        25
```

METHODS AND SYSTEMS FOR POLYNUCLEOTIDE DETECTION

CROSS-REFERENCE TO RELATED APPLICATIONS

This application is a continuation-in-part of U.S. patent application Ser. No. 10/146,720, entitled A METHOD TO ASSEMBLE SPLICE VARIANTS FOR BOTH KNOWN AND PREDICTED GENES, A METHOD FOR VALIDATING THEIR EXPRESSION IN CELLS AND A METHOD OF DISCOVERING NOVEL EXON/EXON EXTENSIONS/TRIMS, filed May 14, 2002, now U.S. Pat. No. 7,340,349 which claims the benefit of U.S. Provisional Patent Application No 60/307,911, entitled A METHOD TO ASSEMBLE SPLICE VARIANTS FOR BOTH KNOWN AND PREDICTED GENES, A METHOD FOR VALIDATING THEIR EXPRESSION IN CELLS AND A METHOD OF DISCOVERING NOVEL EXON/EXON EXTENSIONS/TRIMS, filed Jul. 25, 2001; the Ser. No. 10/146,720 application also claims the benefit of U.S. Provisional Application No. 60/343,298, entitled METHODS OF OLIGO SELECTION AND OPTIMIZATION, filed Dec. 21, 2001; and the Ser. No. 10/146,720 application also claims the benefit of U.S. Provisional Application No. 60/329,914, entitled A METHOD TO ASSEMBLE SPLICE VARIANTS FOR BOTH KNOWN AND PREDICTED GENES, A METHOD FOR VALIDATING THEIR EXPRESSION IN CELLS AND A METHOD OF DISCOVERING NOVEL EXON/EXON EXTENSIONS/TRIMS, filed Oct. 17, 2001, which are hereby incorporated by reference in their entirety.

TECHNICAL FIELD

The described technology relates generally to selecting indicator polynucleotides and to detecting polynucleotides.

BACKGROUND

Polymerase chain reaction (PCR) analyses, nucleotide array experiments, in situ hybridizations, and Southern, Northern and Dot blot experiments attempt to form DNA-DNA, RNA-RNA, or DNA-RNA hybrids. In such experiments, an "indicator polynucleotide," such as an oligonucleotide probe, hybridizes to a polynucleotide that includes a polynucleotide subsequence complementary to the indicator polynucleotide. The "melting temperature," which depends in part upon the nucleotide sequence of the indicator polynucleotide, characterizes the stability of the hybridization product given a set of experimental conditions. The melting temperature is the temperature at which 50% of a given indicator polynucleotide hybridizes to complementary polynucleotides of sufficient abundance. The melting temperature is critical for determining the selectivity and sensitivity of indicator polynucleotides when used as primers in polymerase chain reaction (PCR) experiments, as probes for in situ hybridizations, as probes for nucleotide array experiments, and in Southern, Northern, or Dot blot experiments. If the melting temperature is too low, few indicator polynucleotides will hybridize to their complementary polynucleotides. If the melting temperature is too high, indicator polynucleotides may hybridize to polynucleotides weakly homologous to their complementary polynucleotides. Even with an optimal melting temperature, the formation of hybridization products may be influenced by experimental conditions and the nucleotide sequences of the indicator polynucleotide and the polynucleotides present in the biological sample or environment. It would be desirable to select indicator polynucleotides to maximize hybridization to complementary polynucleotides while minimizing hybridization to other polynucleotides. Also, it would be desirable if the post-hybridization analysis would factor in expected variations due to differing melting temperatures of indicator polynucleotides as well as expected variations due to homologous polynucleotides and other polynucleotides present in the sample or environment.

DETAILED DESCRIPTION

Figure 1:
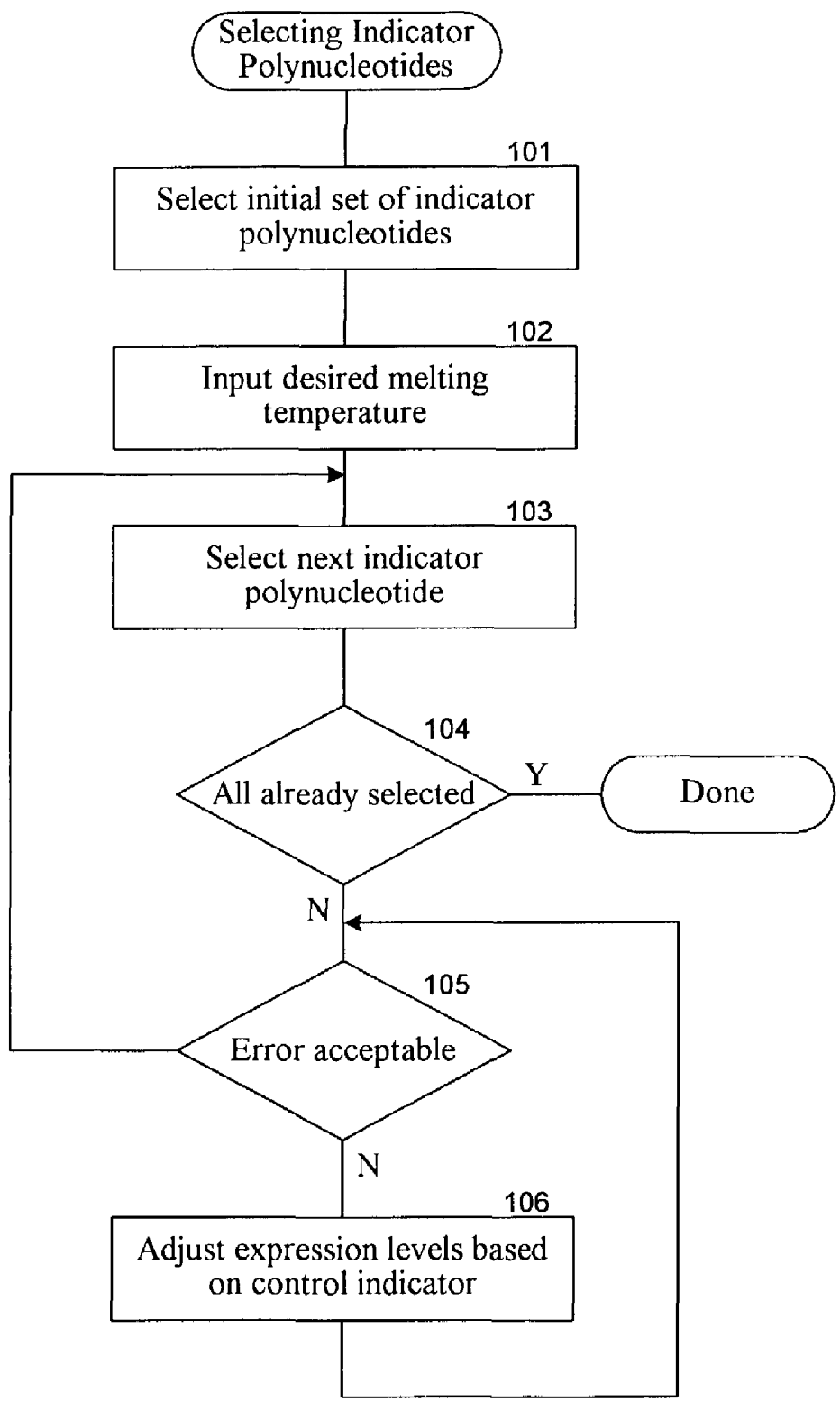
FIG. 1 is a flow diagram illustrating the overall process of selecting indicator polynucleotides to minimize the errors between the actual melting temperatures and the desired melting temperature in one embodiment.

Splice variants of a gene can be broadly classified into two categories: splice variants that use the same reading frames for every exon during translation and those variants that use shifted reading frames for one or more exons. Of these two categories, the first, herein called in-frame variants, are the most interesting from a functional diversity point of view, as they comprise the commonly observed variants and generate variations of the same protein sequences. Variants of the second category, herein called out-of-frame variants, more often result in inactive proteins by introducing pre-mature stop codons and may be useful in linking function with phenotype for a gene in question. In-frame variants can result from an alternative 5' splice site, an alternative 3' splice site, a missing exons, and mutually exclusive exons. Out-of-frame variants can result from retained introns and/or splicing of out-of-frame exon-exon junction.

The present method begins by generating all statistically possible in-frame variants and designing arrays to monitor their expression levels in various tissues. Oligonucleotides (i.e., indicator polynucleotides) corresponding to all exon-exon junctions from all in-frame variants are sensitive in predicting relative expression levels of variants within the same sample and allow identification of new variants that uses novel exons or exon extensions. The present method can also be used to generate all possible out-of-frame variants (with numerous optional constraints).

Optimization techniques for selecting indicator polynucleotides for an experiment and for determining expression levels resulting from the experiment are provided. In one embodiment, the optimization technique corrects for variations in polynucleotide melting temperatures during analysis of the experimental results. The optimization technique selects set of indicator polynucleotides for the experiment. The optimization technique then performs the experiment with the indicator polynucleotides and a sample and identifies the relative amounts of the indicated polynucleotides. The optimization technique then adjusts the relative amounts of the indicated polynucleotides based on melting temperatures associated with the indicator polynucleotides. For example, if one of the indicator polynucleotides has a high melting temperature relative to the hybridization and wash temperatures, then the optimization technique may increase the relative amount of the corresponding indicated polynucleotide to account for the high melting temperature. In an alternate embodiment, the optimization technique includes a control indicator polynucleotide to identify relative amounts of a homologue polynucleotide whose presence is incidentally detected by an indicator polynucleotide designed to detect the presence of a target polynucleotide.

In another embodiment, the optimization technique attempts to minimize the difference between the actual melting temperature of an indicator polynucleotide and a desired melting temperature. When multiple indicator polynucleotides are used in a single experiment, the optimization technique attempts to minimize the overall error resulting from differences in the melting temperatures of the indicator polynucleotides and the desired melting temperature. The optimization technique may modify indicator polynucleotides prior to performing an experiment to reduce the error. The optimization technique may modify an indicator polynucleotide by shifting the location of an indicator polynucleotide to hybridize with upstream or downstream portions of the target polynucleotide. The optimization technique may also vary the lengths of the indicator polynucleotides to minimize the error. When detecting exon-exon junctions, the optimization technique may attempt to balance the melting temperature for each exon portion of the indicator polynucleotide so that the indicator polynucleotide will hybridize to both exons equally. These and another optimization techniques are described more fully in the following.

Measuring Error in Melting Temperatures

In one embodiment, the optimization technique selects an indicator polynucleotide from among multiple possibilities that will minimize an error equation, such as the following distance equation:

$$E^2 = (T_d - T_m)^2 \quad (1)$$

where E is the error, $T_d$ is the desired melting temperature, and $T_m$ is the theoretical or empirical melting temperature of the polynucleotide. Equation 1 is generally referred to as an Euclidean distance measure. The indicator polynucleotide with the smallest error may be the best choice.

When multiple indicator polynucleotides are to be used in the same experiment, the optimization technique selects indicator polynucleotides that tend to minimize the overall error in melting temperatures. In one embodiment, the optimization technique calculates the error according to the following equation.

$$E_t^2 = E_1^2 + E_2^2 + \ldots + E_n^2 \quad (2)$$

where $E_t$ is the total error, $E_i$ is the error from the ith polynucleotide, and n is the number of indicator polynucleotides.

A more general formulation of error equation 1 that applies to a single polynucleotide is the following equation:

$$E = f(T_d, T_m) \quad (3)$$

where f is any arbitrary error function. The substitution of equation 3 into equation 2 for multiple polynucleotides results in the following equation:

$$E_t = g(f(T_d, T_{m1}), f(T_d, T_{m2}), \ldots, f(T_d, T_{mn})) \quad (4)$$

where g is a function that combines the individual error measures of the n indicator polynucleotides. When an experimental design includes constraints, such as which genes, exons, or exon-exon junctions the indicator polynucleotides identify, the optimization technique selects those indicator polynucleotides that minimize the value of $E_t$ given the desired melting temperature $T_d$.

To illustrate the error calculation, an example nucleotide array experiment involving indicator polynucleotides for each exon and exon-exon junction of a transcript of the gene CD44 with the GenBank locus name XM_030326, which contains 18 exons and 17 exon-exon junctions, is used. One indicator polynucleotide selection technique might select indicator polynucleotides with a length of 20 bases. Each indicator polynucleotide for an exon is selected to hybridize to the center of the exon, and each indicator polynucleotide for an exon-exon junction is selected to hybridize to 10 bases on each side of the exon-exon junction. The selected indicator polynucleotides are presented in the following table:

TABLE 1

| SEQ ID NO | Junction/Exon | Melting Temp ° C. | Sequence |
| --- | --- | --- | --- |
| SEQ ID NO: 1 | E1 | 62.030003 | cgcgcccagggatcctccag |
| SEQ ID NO: 2 | J1-2 | 22.0 | gcgcagatcgatttgaatat |
| SEQ ID NO: 3 | E2 | 59.980003 | ggaggccgctgacctctgca |
| SEQ ID NO: 4 | J2-3 | 30.0 | agacctgcaggtatgggttc |
| SEQ ID NO: 5 | E3 | 53.83 | tgcagcaaacaacacagggg |
| SEQ ID NO: 6 | J3-4 | 32.0 | aatgcttcagctccacctga |
| SEQ ID NO: 7 | E4 | 53.83 | agtcacagacctgcccaatg |
| SEQ ID NO: 8 | J4-5 | 24.0 | attaccataactattgttaa |
| SEQ ID NO: 9 | E5 | 55.880005 | gctcctccagtgaaaggagc |
| SEQ ID NO: 10 | J5-6 | 28.0 | cctgctaccactttgatgag |
| SEQ ID NO: 11 | E6 | 51.780003 | cctgggattggttttcatgg |
| SEQ ID NO: 12 | J6-7 | 30.0 | caaatggctggtacgtcttc |
| SEQ ID NO: 13 | E7 | 49.730003 | gatgaaagagacagacacct |
| SEQ ID NO: 14 | J7-8 | 28.0 | tccagcaccatttcaaccac |
| SEQ ID NO: 15 | E8 | 55.880005 | tggacccagtggaacccaag |
| SEQ ID NO: 16 | J8-9 | 28.0 | aggatgactgatgtagacag |
| SEQ ID NO: 17 | E9 | 53.83 | aagcacaccctcccctcatt |
| SEQ ID NO: 18 | J9-10 | 32.0 | acaagcacaatccaggcaac |
| SEQ ID NO: 19 | E10 | 51.780003 | ggtttggcaacagatggcat |

TABLE 1-continued

| SEQ ID NO | Junction/ Exon | Melting Temp ° C. | Sequence |
|---|---|---|---|
| SEQ ID NO: 20 | J10-11 | 34.0 | gggacagctgcagcctcagc |
| SEQ ID NO: 21 | E11 | 49.730003 | gacagttcctggactgattt |
| SEQ ID NO: 22 | J11-12 | 28.0 | agaaggatggatatggactc |
| SEQ ID NO: 23 | E12 | 47.68 | aatccaaacacaggtttggt |
| SEQ ID NO: 24 | J12-13 | 28.0 | atgacaacgcagcagagtaa |
| SEQ ID NO: 25 | E13 | 47.68 | gaaggcttggaagaagataa |
| SEQ ID NO: 26 | J13-14 | 26.0 | acatcaagcaataggaatga |
| SEQ ID NO: 27 | E14 | 51.780003 | acgaaggaaagcaggacctt |
| SEQ ID NO: 28 | J14-15 | 30.0 | tccttatcaggagaccaaga |
| SEQ ID NO: 29 | E15 | 57.930004 | cagtgggggtcccatacca |
| SEQ ID NO: 30 | J15-16 | 30.0 | gaatcagatggacactcaca |
| SEQ ID NO: 31 | E16 | 53.83 | ggagcaaacacaacctctgg |
| SEQ ID NO: 32 | J16-17 | 28.0 | caaattccagaatggctgat |
| SEQ ID NO: 33 | E17 | 49.730003 | ccttggctttgattcttgca |
| SEQ ID NO: 34 | J17-18 | 34.0 | gtcgaagaaggtgtgggcag |
| SEQ ID NO: 35 | E18 | 53.83 | tcgttccagttcccacttgg |

The NCBI locus name and version for the genomic sequence containing the CD44 gene is NT_024229.8. The NCBI locus name and version for the mRNA sequence of the CD44 transcript is XM_030326.3. The identifiers E1, E2, E3, and etc. identify indicator polynucleotides for exon 1, exon 2, exon 3, and etc. The identifiers J1-2, J2-3, and etc. identify indicator polynucleotides for the exon-exon junction between exon 1 and exon 2, the exon-exon junction between exon 2 and exon 3, and etc. The melting temperatures are theoretical melting temperatures of the indicator polynucleotide, calculated according to the following equation:

$$T_m = 64.9° C. + 41° C. * (GC - 16.4)/L \quad (5)$$

where L is the length of the target polynucleotide and GC is the GC content. One skilled in the art will appreciate the theoretical melting temperature can be calculated using various well-known equations. The calculated melting temperature varies from a low of 22° C. to a high of 62.03° C. in this example. This wide range of melting temperatures will lead to substantial variation in the number of polynucleotides that hybridize to instances of a given indicator polynucleotides in an experiment with fixed hybridization and washing temperatures. For example, in an experiment with a sample containing CD44 using a standard protocol with a hybridization temperature of 52° C. and a washing temperature of 52° C., the indicator polynucleotides with melting temperatures under 52° C. will form and retain hybridization products less frequently than those with melting temperatures above 52° C. In general, indicator polynucleotides with low calculated melting temperatures may not bind to their target exons or exon-exon junctions with any measurable strength above a background level. The error with a target temperature of 52° C. is calculated using equation 2 in the following:

$$E_t^2 = (52-62.03)^2 + (52-22)^2 + \ldots + (52-53.83)^2 = (97.46)^2$$

Modifying Indicator Polynucleotides to Reduce Errors in Melting Temperatures

The optimization technique can optimize an indicator polynucleotide prior to running the experiment. The optimization technique may optimize indicator polynucleotides by shifting the location of the indicator polynucleotides slightly upstream or downstream within their respective RNAs. For example, the optimization technique can select indicator polynucleotides for exons from any base range within the exon that the indicator polynucleotide identifies, using any selection criteria, such as GC content. Alternatively, the optimization technique can optimize indicator polynucleotides by varying their lengths. For example, rather than selecting only indicator polynucleotides with a length of 20 bases, the optimization technique may select indicator polynucleotides of varying lengths to reduce the error measure for each indicator polynucleotide. These various optimizations may be used alone or in conjunction with other indicator polynucleotide selection, analytical correction, or other optimizations. When varying the length of the indicator polynucleotides for the same CD44 transcript, without using other indicator polynucleotide selection or optimizations, the resulting indicator polynucleotide are shown in the following:

TABLE 2

| SEQ ID NO | Junction/ Exon | Melting Temp ° C. | Sequence |
|---|---|---|---|
| SEQ ID NO: 36 | E1 | 51.062504 | gcccagggatcctcca |
| SEQ ID NO: 37 | J1-2 | 52.258335 | cgcagatcgatttgaatataacct |
| SEQ ID NO: 38 | E2 | 51.062504 | aggccgctgacctctg |
| SEQ ID NO: 39 | J2-3 | 53.24737 | gacctgcaggtatgggttc |
| SEQ ID NO: 40 | E3 | 51.089478 | tgcagcaaacaacacaggg |
| SEQ ID NO: 41 | J3-4 | 51.089478 | aatgcttcagctccacctg |
| SEQ ID NO: 42 | E4 | 51.089478 | agtcacagacctgcccaat |
| SEQ ID NO: 43 | J4-5 | 51.653847 | caattaccataactattgttaaccgt |
| SEQ ID NO: 44 | E5 | 53.24737 | ctcctccagtgaaaggagc |
| SEQ ID NO: 45 | J5-6 | 51.780003 | cctgctaccactttgatgag |

TABLE 2-continued

| SEQ ID NO | Junction/Exon | Melting Temp °C. | Sequence |
|---|---|---|---|
| SEQ ID NO: 46 | E6 | 52.97273 | cctgggattggttttcatggtt |
| SEQ ID NO: 47 | J6-7 | 51.780003 | caaatggctggtacgtcttc |
| SEQ ID NO: 48 | E7 | 51.109093 | aagatgaaagagacagacacct |
| SEQ ID NO: 49 | J7-8 | 51.780003 | ccagcaccatttcaaccaca |
| SEQ ID NO: 50 | E8 | 52.600002 | ggacccagtggaacccaa |
| SEQ ID NO: 51 | J8-9 | 51.7087 | aaggatgactgatgtagacagaa |
| SEQ ID NO: 52 | E9 | 51.876472 | gcacaccctcccctcat |
| SEQ ID NO: 53 | J9-10 | 52.404762 | tacaagcacaatccaggcaac |
| SEQ ID NO: 54 | E10 | 51.780003 | ggtttggcaacagatggcat |
| SEQ ID NO: 55 | J10-11 | 51.876472 | ggacagctgcagcctca |
| SEQ ID NO: 56 | E11 | 52.404762 | gacagttcctggactgatttc |
| SEQ ID NO: 57 | J11-12 | 52.97273 | aagaaggatggatatggactcc |
| SEQ ID NO: 58 | E12 | 51.109093 | caaatccaaacacaggtttggt |
| SEQ ID NO: 59 | J12-13 | 51.7087 | aatgacaacgcagcagagtaatt |
| SEQ ID NO: 60 | E13 | 51.7087 | gaaggcttggaagaagataaaga |
| SEQ ID NO: 61 | J13-14 | 51.7087 | gacatcaagcataggaatgatg |
| SEQ ID NO: 62 | E14 | 51.089478 | acgaaggaaagcaggacct |
| SEQ ID NO: 63 | J14-15 | 50.452385 | ttccttatcaggagaccaaga |
| SEQ ID NO: 64 | E15 | 51.062504 | tggggggtcccatacc |
| SEQ ID NO: 65 | J15-16 | 51.109093 | tgaatcagatggacactcacat |
| SEQ ID NO: 66 | E16 | 51.089478 | ggagcaaacacaacctctg |
| SEQ ID NO: 67 | J16-17 | 52.97273 | ccaaattccagaatggctgatc |
| SEQ ID NO: 68 | E17 | 52.404762 | ccttggctttgattcttgcag |
| SEQ ID NO: 69 | J17-18 | 52.600002 | gtcgaagaaggtgtgggc |
| SEQ ID NO: 70 | E18 | 51.089478 | tcgttccagttcccacttg |

Since the calculated polynucleotide melting temperatures have a small range, from 50.45° C. to 52.97° C. (rather than 22° C. to 62.03° C.), the error measure Et of 4.51 (rather than 97.46) is also small. This varying of the lengths of the indicator polynucleotides has eliminated over 95% of the error encountered when the indicator polynucleotides were selected as shown in Table 1.

FIG. 1 is a flow diagram illustrating the overall process of selecting indicator polynucleotides to minimize the errors between the actual melting temperatures and the desired melting temperature in one embodiment. In block 101, the technique selects an initial set of indicator polynucleotides. In block 102, the technique inputs the desired melting temperature of the indicator polynucleotides. In blocks 103-105, the technique modifies each indicator polynucleotide to minimize its error. In block 103, the technique selects the next indicator polynucleotide. In decision block 104, if all the indicator polynucleotides have already been selected, then the technique completes, else the technique continues at block 105. In decision block 105, if the error between actual melting temperature of the selected indicator polynucleotide and the desired melting temperature is acceptable, then the technique selects the next indicator polynucleotide, else the technique continues at block 106. In block 106, the technique modifies the selected indicator polynucleotide using one or more of the described techniques (e.g., adjusting the length of the indicator polynucleotide or moving the indicator polynucleotide upstream or downstream) and then continues at a block 105.

One skilled in the art will recognize that the error Et may be further reduced in a variety of ways, such as by introducing molecules other than the bases A, C, G, or T with different binding characteristics. Such bases may be appended, prepended, inserted, or selectively substituted within the indicator polynucleotides.

CD44 is known to have several splice variants. For example, the transcript used above contains several exons not present in other splice forms of CD44. In particular, J6-7 does not exist in some species of CD44. Instead, E6 joins with a later exon E7', yielding J6-7'. The RNA transcript containing the J6-7 is referred to as $R^1$, and the RNA transcript containing J6-7' is referred to as $R^2$.

When using indicator polynucleotides to identify exon-exon junctions, binding may be less specific than desired if polynucleotides bind to one or the other half of an indicator polynucleotide. For example, if J6-7 is not present in a given sample, but E6 is present (because a different splice form of the gene is present in that sample), then an indicator polynucleotide for J6-7 may hybridize to E6 even though E6 is not joined to E7 in the splice variant in the sample. The hybridization, however, will likely be weaker than if a splice variant containing J6-7 was present. The expression levels may be measured as $H(E6)=1069$ $H(J6-7)=388$ where H(E6) is the measured expression level of E6 in the experiment and H(J6-7) is the measured expression level of J6-7. These measured expression may represent the following scenarios:

1. $R^1$ is present but $R^2$ is not present.
2. $R^1$ and $R^2$ are both present.
3. Neither $R^1$ nor $R^2$ is present, but another splice variant $R^3$ is present. $R^3$ contains both E6 and E7, but not J6-7, because some alternate splicing event or events occurs between E6 and E7.

Techniques described in U.S. patent application Ser. No. 10/146,720, entitled "Method and System for Identifying Splice Variants of a Gene," can be used to differentiate these scenarios. Those techniques assign an expected expression level to J6-7 in the presence of $R^1$, in the presence of $R^2$, and in the presence of $R^3$. For example, if there are indicator polynucleotides for E6, E7, and J6-7, then a matrix M with a column for each expected splice variant (e.g., $R^1$, $R^2$ and $R^3$) and a row for each indicator polynucleotide (e.g., E6, E7, and J6-7) is created. The values in the matrix correspond to the expected expression level for the target polynucleotides. When the partial expression levels are not expected, the matrix might-look like the following:

$$M = \begin{array}{c} \phantom{M=}\begin{array}{ccc} R^1 & R^2 & R^3 \end{array} \\ \left[\begin{array}{ccc} 1 & 1 & 1 \\ 1 & 0 & 0 \\ 1 & 0 & 1 \end{array}\right] \begin{array}{c} E6 \\ J6\text{-}7 \\ E7 \end{array} \end{array}$$

If the indicator polynucleotide for J6-7, however, weakly binds in the presence of a different splice site, J6-7', a correction can be applied. The values in the correction matrix can be calculated or empirically derived. The values can be empirically derived by performing a hybridization experiment containing J6-7' but not J6-7. The correction matrix may be derived using one or more samples containing antisense polynucleotides. A sample could include antisense polynucleotides for J6 or J7 or both. ("J6" refers to the portion of an indicator polynucleotide for a J6-X junction that is used to identify the E6 portion of the junction.) For example, an antisense polynucleotide for J6 might contain the complementary polynucleotide for J6. Alternatively, the antisense polynucleotide might contain the complementary polynucleotide for J6 appended to a sequence of some additional number of bases, perhaps chosen randomly. In yet another scenario, the antisense polynucleotide might contain J6 with J7 prepended. After the hybridization experiments, the following expression values may result:

$H(J6\text{-}7|J6)=556$ $H(J6\text{-}7|J7)=310$ $H(J6\text{-}7|J6\text{-}7)=1544$ $H(J6\text{-}7|J6, J7)=756$ where $H(J6\text{-}7|J6)$ is the empirically derived expression level of the indicator polynucleotide for J6-7 in the presence of a sample containing antisense polynucleotides for J6, $H(J6\text{-}7|J7)$ is the expression level of J6-7 in the presence of a sample containing antisense polynucleotides for J7, $H(J6\text{-}7|J6\text{-}7)$ is the ordinary expression level of J6-7 in the presence of antisense polynucleotides for J6-7, and $H(J6\text{-}7|J6, J7)$ is the expression level of J6-7 in the presence of separate antisense polynucleotides for J6 and J7. The expression values are not independent and are preferably measured in separate hybridization experiments. If more than one expression level is measured in the same experiment, the individual values can be solved using a system of linear equations, a least squares equation, or another deconvolution method.

Once the expression levels have been determined either empirically or theoretically, the values in the matrix M could be determined using an equation such as:

$$M_{I,j}=H(P_i|R_j)/H(P_i) \tag{6}$$

where $M_{I,j}$ is a coefficient matrix, $P_i$ is an indicator polynucleotide that identifies a subsequence of RNA transcript $R_j$, $H(P_i|R_j)$ is the expression level of indicator polynucleotide $P_i$ given that RNA $R_j$ is expressed, and $H(P_i)$ is the expression level of the hybridization product of indicator polynucleotide i. The solution to this equation is:

$M_{2,1}=H(J6\text{-}7|J6\text{-}7)/H(J6\text{-}7|J6\text{-}7)=1544/1544=1$ $M_{2,2}=H(J6\text{-}7|J6)/H(J6\text{-}7|J6\text{-}7)=556/1544=0.36$ $M_{2,3}=H(J6\text{-}7|J6,J7)/H(J6\text{-}7|J6\text{-}7)=756/1544=0.49$ In this example, $H(J6\text{-}7|J6\text{-}7)$ is the expression of the indicator polynucleotide for J6-7 given RNA containing J6-7 is present. The remaining matrix elements all have a value of 1, for the same reason as $M_{2,1}$. The resulting matrix M is:

$$M = \begin{array}{c} \phantom{M=}\begin{array}{ccc} R^1 & R^2 & R^3 \end{array} \\ \left[\begin{array}{ccc} 1 & 1 & 1 \\ 1 & 0.36 & 0.49 \\ 1 & 0 & 1 \end{array}\right] \begin{array}{c} E6 \\ J6\text{-}7 \\ E7 \end{array} \end{array}$$

The value 0.36 indicates that the indicator polynucleotide for J6-7 will yield a relative expression level of 0.36 times the full value if $R^2$ is present, and the other two splice variants are not present. The expression level is non-zero in this case because the indicator polynucleotide for J6-7 will hybridize weakly in the presence of E6 even if J6-7 is not present. The value 0.49 indicates that the indicator polynucleotide for J6-7 will yield a relative expression level of 0.49 times the full value if $R^3$ is present and the other two splice variants are not present. The value for J6-7 in $R^3$ is larger than the corresponding value in $R^2$ because the indicator polynucleotide will hybridize weakly to both E6 and E7 rather than only to E6.

Modifying a Junction Indicator Polynucleotide to Balance Its Melting Temperature The indicator polynucleotide for J6-7 consists of a portion J6 that identifies the 3' end of E6 as well as a portion J7 that identifies the 5' end of E7. Each of these portions has its own melting temperature. In other words, the indicator polynucleotide for J6-7 will hybridize to E6 based on the melting temperature of J6 even if J6-7 is not present in the sample. Likewise, the indicator polynucleotide will hybridize to E7 based on the melting temperature of J7 even if J6-7 is not present in the sample. In one embodiment, the optimization technique balances the melting temperature of each exon portion of a junction indicator polynucleotide.

A full set of exon-exon junction indicator polynucleotides with a length of 30 bases for CD44 selected to have 15 bases for each exon is shown in the following:

TABLE 3

| SEQ ID No | Junction/ Exon | Melting Temp ° C. | Left Melting Temp ° C. | Right Melting Temp ° C. | Sequence |
|---|---|---|---|---|---|
| SEQ ID NO: 71 | J1-2 | 61.620003 | 50.140003 | 28.273338 | gcctggcgcagatcgatttgaatataacct |
| SEQ ID NO: 72 | J2-3 | 60.253334 | 39.20667 | 36.473335 | atttgagacctgcaggtatgggttcataga |
| SEQ ID NO: 73 | J3-4 | 62.986668 | 39.20667 | 41.940002 | gcttcaatgcttcagctccacctgaagaag |
| SEQ ID NO: 74 | J4-5 | 57.520004 | 33.74 | 36.473335 | gaccaattaccataactattgttaaccgtg |
| SEQ ID NO: 75 | J5-6 | 61.620003 | 41.940002 | 36.473335 | gaatccctgctaccactttgatgagcacta |
| SEQ ID NO: 76 | J6-7 | 58.88667 | 39.20667 | 33.74 | caacacaaatggctggtacgtcttcaaata |
| SEQ ID NO: 77 | J7-8 | 61.620003 | 39.20667 | 39.20667 | ttatctccagcaccatttcaaccacaccac |
| SEQ ID NO: 78 | J8-9 | 60.253334 | 41.940002 | 33.74 | ccacaaggatgactgatgtagacagaaatg |
| SEQ ID NO: 79 | J9-10 | 60.253334 | 33.74 | 41.940002 | attctacaagcacaatccaggcaactccta |
| SEQ ID NO: 80 | J10-11 | 65.72 | 44.673336 | 41.940002 | caacagggacagctgcagcctcagctcata |
| SEQ ID NO: 81 | J11-12 | 62.986668 | 41.940002 | 39.20667 | caggaagaaggatggatatggactccagtc |
| SEQ ID NO: 82 | J12-13 | 58.88667 | 36.473335 | 36.473335 | tttcaatgacaacgcagcagagtaattctc |
| SEQ ID NO: 83 | J13-14 | 58.88667 | 39.20667 | 33.74 | ctctgacatcaagcaataggaatgatgtca |
| SEQ ID NO: 84 | J14-15 | 60.253334 | 36.473335 | 39.20667 | atcgttccttatcaggagaccaagacacat |
| SEQ ID NO: 85 | J15-16 | 61.620003 | 36.473335 | 41.940002 | gatctgaatcagatggacactcacatggga |
| SEQ ID NO: 86 | J16-17 | 61.620003 | 41.940002 | 36.473335 | caccccaaattccagaatggctgatcatct |
| SEQ ID NO: 87 | J17-18 | 62.986668 | 39.20667 | 41.940002 | caacagtcgaagaaggtgtgggcagaagaa |

The melting temperature is the calculated melting temperature of the complete indicator polynucleotide, the left melting temperature is the calculated melting temperature of the first 15 bases of the indicator polynucleotide which detect the 3' end of the first exon in each junction, and the right melting temperature is the calculated melting temperature of the last 15 bases of the indicator polynucleotide which detect the 5' end of the second exon in each junction. The variation between the two sides of a given indicator polynucleotide may be considerable; the difference between the left and right melting temperature for the same indicator polynucleotide is as large as 21.87° C. for J1-2.

The temperature difference in J6-7 is approximately 5.5° C. The expected result of the difference is that the indicator polynucleotide will yield a larger expression value if E6 is present without J6-7 than if E7 is present without J6-7. A similar effect will be observed to varying degrees for all of the indicator polynucleotides. In one embodiment, the optimization technique corrects for these effects using the linear equations presented above. For example, different values for a transcript containing E6 but not E7 than for a transcript containing E7 but not E6 may be used. The corrected matrix might look like this:

$$M^c = \begin{array}{c} R^1 \ R^2 \ R^3 \\ \begin{bmatrix} 1.00 & 1.00 & 0.00 \\ 1.00 & 0.41 & 0.29 \\ 1.00 & 0.00 & 1.00 \end{bmatrix} \begin{array}{l} E6 \\ J6\text{-}7 \\ J7 \end{array} \end{array}$$

where $R^2$ is a transcript containing E6 but not E7 and $R^3$ is a transcript containing E7 but not E6. However, it would be desirable to minimize the need to correct experimental results in this way, since it is generally desirable to minimize the number of experimental parameters that vary in the same experiment. The optimization technique minimizes or eliminates the need for this correction by balancing the melting temperature on each side of the exon-exon junction, so that the melting temperatures of indicator polynucleotide portions J6 and J7 are close to equal.

An optimization equation for error from imbalanced melting temperature using Euclidean distance can be written as:

$$E_x^2 = (T_{ia} - T_{ib})^2 \quad (7)$$

where $E_x$ is the error from imbalance in melting temperature, $T_{ia}$ is the calculated or empirical melting temperature of the portion of the indicator polynucleotide which identifies the 3' end of the first exon, and $T_{ib}$ is the calculated melting temperature of the portion of the indicator polynucleotide which identifies the 5' end of the second exon. If the indicator polynucleotide does not identify an exon-exon junction, the error is zero. The total error in the experiment then is given by:

$$E_{xt}^2 = E_{x1}^2 + E_{x2}^2 + \ldots + E_{xn}^2 \quad (8)$$

where $E_{xt}$ is the total error from multiple indicator polynucleotides as a result of temperature imbalance in indicator polynucleotides that identify exon-exon junctions. One skilled in the art will appreciate that error metrics other than Euclidean distance may be used.

In one embodiment, the optimization technique considers both temperature balancing in exon-exon junction indicator polynucleotides and total indicator polynucleotide melting temperature, which can be represented by the following equation:

$$E_{jt} = k_1 E + k_2 E_x \quad (9)$$

where $E_{jt}$ is the joint error measure, E is given by equation 1, $E_x$ is given by equation 7, and $k_1$ and $k_2$ are constants. The total joint error measure can be represented by the following equation:

$$E_{jt} = E_{j1} + E_{j2} + \ldots + E_{jn} \quad (10)$$

where $E_{jt}$ is the total error from both temperature imbalance in exon-exon junction indicator polynucleotides and each $E_{ji}$ is the error for each individual indicator polynucleotide i calculated using equation 9. One skilled in the art will appreciate that error metrics other than Euclidea distance can be used and that equations 7-10 can be generalized as equations 3 and 4 were generalized.

The exon-exon junction indicator polynucleotides selected from CD44 according to equations 7-10, using a desired total melting temperature $T_d = 60°$ C. and $k_1 = k_2 = 1.0$ are shown in the following:

TABLE 4

| SEQ ID No | Junction/ Exon | Melting Temp ° C. | Left Melting Temp ° C. | Right Melting Temp ° C. | Sequence |
|---|---|---|---|---|---|
| SEQ ID NO: 88 | J2-2 | 59.921432 | 38.0 | 37.405884 | ggcgcagatcgatttgaatataacctgc |
| SEQ ID NO: 89 | J2-3 | 59.921432 | 38.0 | 38.25 | tgagacctgcaggtatgggttcatagaa |
| SEQ ID NO: 90 | J3-4 | 61.255558 | 39.20667 | 38.0 | gcttcaatgcttcagctccacctgaag |
| SEQ ID NO: 91 | J4-5 | 59.59412 | 39.81765 | 39.81765 | tggaccaattaccataactattgttaac-cgtgat |
| SEQ ID NO: 92 | J5-6 | 59.737038 | 37.37143 | 38.0 | aatccctgctaccactttgatgagcac |
| SEQ ID NO: 93 | J6-7 | 60.40323 | 39.20667 | 38.25 | caacacaaatggctggtacgtcttcaaatac |
| SEQ ID NO: 94 | J7-8 | 59.737038 | 37.37143 | 38.0 | tatctccagcaccatttcaaccacacc |
| SEQ ID NO: 95 | J8-9 | 60.253334 | 37.37143 | 38.25 | cacaaggatgactgatgtagacagaaatgg |
| SEQ ID NO: 96 | J9-10 | 59.921432 | 38.25 | 38.0 | cattctacaagcacaatccaggcaactc |
| SEQ ID NO: 97 | J10-11 | 59.980003 | 34.0 | 34.0 | gggacagctgcagcctcagc |
| SEQ ID NO: 98 | J11-12 | 59.737038 | 37.37143 | 38.0 | aggaagaaggatggatatggactccag |
| SEQ ID NO: 99 | J12-13 | 58.88667 | 36.473335 | 36.473335 | tttcaatgacaacgcagcagagtaattctc |
| SEQ ID NO: 100 | J13-14 | 60.54375 | 39.20667 | 39.81765 | ctctgacatcaagcaataggaatgatgtcaca |

TABLE 4-continued

| SEQ ID No | Junction/ Exon | Melting Temp °C. | Left Melting Temp °C. | Right Melting Temp °C. | Sequence |
|---|---|---|---|---|---|
| SEQ ID NO: 101 | J14-15 | 59.737038 | 38.0 | 37.37143 | cgttccttatcaggagaccaagacaca |
| SEQ ID NO: 102 | J15-16 | 61.506897 | 40.8125 | 40.0 | ggatctgaatcagatggacactcacatgg |
| SEQ ID NO: 103 | J16-17 | 60.093105 | 37.37143 | 36.473335 | accccaaattccagaatggctgatcatct |
| SEQ ID NO: 104 | J17-18 | 59.324 | 38.0 | 38.0 | acagtcgaagaaggtgtgggcagaa |

Variations between the left melting temperature and right melting temperature values has decreased significantly; the maximum difference between left melting temperature and right melting temperature is now only approximately 0.95° C. The temperature balancing technique has eliminated over 95% of the variability in melting temperature between the two portions of each exon-exon junction indicator polynucleotide as compared to the indicator polynucleotide selection technique. The melting temperature of a fixed-length indicator polynucleotide can be balanced by decreasing the length of one exon's portion and increasing the length of the other exon's portion. For example, if the length of the indicator polynucleotide for a junction is 20 and the length of each portion is 10, then the length of one portion may be decreased to 8 and the length of the other portion might be increased to 12 to balance the melting temperature, keeping the overall length at 20. Corrections can be applied to experimental results, as described above, to further reduce the variability.

Correcting Analytically for Variations in Melting Temperature

Figure 2:
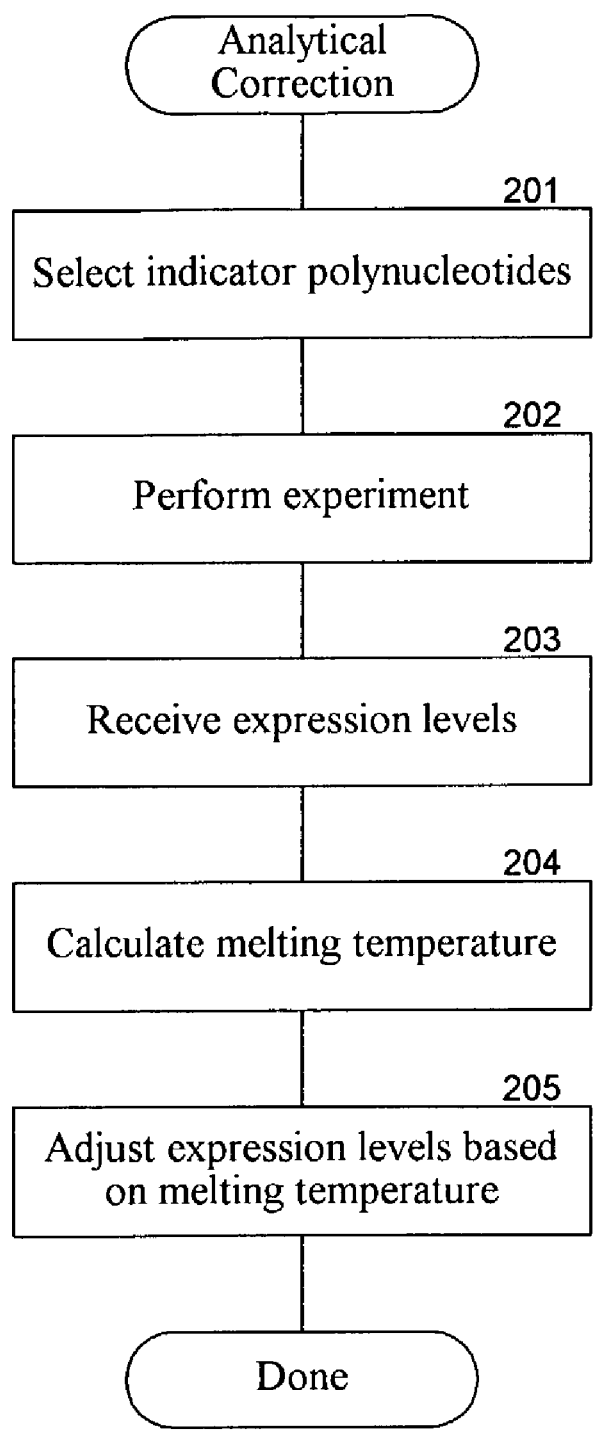
FIG. 2 is a flow diagram illustrating the overall process of analytically correcting for variations in melting temperatures in one embodiment.

In one embodiment, the optimization technique corrects for variations in polynucleotide melting temperatures during analysis of the experimental results. This correction can be used whether or not an optimal set of indicator polynucleotides is selected as described above. The optimization technique adjusts the detected expression levels of the polynucleotides based on theoretical and desired melting temperatures. FIG. 2 is a flow diagram illustrating the overall process of analytically correcting for variations in melting temperatures in one embodiment. The steps of the processes illustrated by the flow diagrams may be controlled by, performed with the assistance of, or performed by a computer system. One skilled in the art will appreciate that various steps may be performed manually. In block 201, the technique selects the indicator polynucleotides that are to be used to identify target polynucleotides in a sample. In block 202, the technique performs the hybridization experiment, for example, using nucleotide array technology. In block 203, the technique receives the resulting expression levels from the experiment. In block 204, the technique calculates or inputs the melting temperature for each of the indicator polynucleotides. In block 205, the technique adjusts the expression levels based on the melting temperature for each of the indicator polynucleotides and temperature (e.g., hybridization temperature or wash temperature) at which the experiment was performed to give the final calculated expression levels for the experiment. One example analysis technique is described in U.S. patent application Ser. No. 10,146,720, filed on May 14, 2002 and entitled "Method and System for Identifying Splice Variants of a Gene," which is hereby incorporated by reference. That splice variants analysis calculates the expression levels according to the following equation:

$$S=MH \quad (11)$$

where S is a solution matrix of expression levels with a row for each expected RNA transcript and a column for each experiment, M is a matrix of coefficients in which each column corresponds to an expected RNA transcript and each row corresponds to an indicator polynucleotide in the experiment (each coefficient indicates the relative expected expression level of the indicator polynucleotide for the expected RNA transcript), and H is a matrix in which each of the columns corresponds to expression values derived from an expression array experiment. Because of experimental noise, an exact solution to this equation may not exist. The splice variants analysis can find an approximation using a variety of Techniques such as a least squares regression using the following equation:

$$S=(MM^T)^{-1}M^TH \quad (12)$$

where $M^T$ is the transpose of M. The values in the coefficient matrix M can be represented by the following equation:

$$M_{i,j}=L(P_i|R_j) \quad (13)$$

where $M_{i,j}$ is the matrix element in the ith row and jth column and $L(P_i|R_j)$ defines a coefficient for indicator polynucleotide P (in the ith row of M) given that the expected RNA transcript R (in the jth column of M) is present in a sample.

If all indicator polynucleotides that identify subsequences of R are expected to be expressed at an identical level when R is present in the sample, and all indicator polynucleotides that do not identify subsequences of R are expected not to be expressed at all, matrix M might consist entirely of zeros and ones. The matrix M for two splice variants of CD44, $R^1$ and $R^2$, is represented by the following:

$$M = \begin{array}{cc} R^1 & R^2 \\ \begin{array}{|cc|} \hline 1 & 1 \\ 1 & 1 \\ 1 & 1 \\ 1 & 1 \\ 1 & 1 \\ 1 & 1 \\ 1 & 0 \\ 1 & 0 \\ 1 & 0 \\ 1 & 0 \\ 1 & 0 \\ 1 & 0 \\ 0 & 1 \\ 1 & 0 \\ 1 & 1 \\ 1 & 1 \\ 1 & 1 \\ 1 & 1 \\ 1 & 1 \\ 1 & 1 \\ 1 & 1 \\ 1 & 1 \\ 1 & 1 \\ \hline \end{array} & \begin{array}{l} E1 \\ E2 \\ E3 \\ E4 \\ E5 \\ E6 \\ J6\text{-}7 \\ E7 \\ J7\text{-}8 \\ E8 \\ J8\text{-}9 \\ E9 \\ J6\text{-}10 \\ J9\text{-}10 \\ E10 \\ E11 \\ E12 \\ E13 \\ E14 \\ E15 \\ E16 \\ E17 \\ E18 \end{array} \end{array}$$

The value of 0 indicates the expected expression level will be zero if the target polynucleotide.g., J6-10) is not present in the sample. The uniform value of 1 indicates the expected expression levels of all other indicator polynucleotides will be equal if the expected RNA transcript is present in the sample. The indicator polynucleotides, however, may identify their target polynucleotides at varying expression levels because of variations in the melting temperature of the indicator polynucleotides.

In one embodiment, the optimization technique adjusts the detected expression levels to account for the variations in melting temperatures. Continuing with the CD44 gene example, the calculated melting temperatures are Used to scale the expected expression levels in matrix M. If the expected expression levels varied linearly with respect to temperature, then the expected expression levels can be adjusted according to the following equation:

$$M_{i,j} = T_i/T_d \quad (14)$$

where $M_{i,j}$ is the element in the ith row and jth column of the matrix M, $T_i$ is the expected melting temperature of the indicator polynucleotide corresponding to row i, and $T_d$ is the desired melting temperature for use in the experiment. If the melting temperature is 62.03 and the desired melting temperature is 52, then the adjusted expression level would be 1.19 (i.e., 62.02/52).

Alternatively, the optimization technique performs the correction by adjusting the detected expression levels of matrix H, rather than adjusting the coefficients of matrix M. If the detected expression level varied linearly with respect to temperature, the detected expression levels can be adjusted according to the following equation:

$$H'_{i,j} = H_{i,j} T_d/T_i \quad (15)$$

where $H_{i,j}$ is the detected expression level for indicator polynucleotide i in experiment j, $H'_{i,j}$ is the corrected expression level, $T_i$ is the expected melting temperature of the indicator polynucleotide corresponding to row i, and $T_d$ is the desired melting temperature. If the melting temperature is 62.03, the desired melting temperature is 52, and the detected expression level is 11,869, then the adjusted expression level is 9950 (i.e., 11,869*52/62.03).

Since expected expression levels will likely vary with respect to temperature according to an equation that is more complex than a linear equation, the optimization technique in one embodiment may apply a correction based on one or more empirical hybridization experiments. One such experiment creates a sample consisting of synthesized polynucleotides to bind to indicator polynucleotides on a nucleotide array. The optimization technique then calculates the expected expression levels of matrix M according to the following equation:

$$M_{i,j} = kH_i \quad (16)$$

where $M_{i,j}$ is the element in the ith row and jth column of the matrix M, Hi is an empirically derived expression level for the indicator polynucleotide i from a hybridization experiment, and k is a constant. For example, if the expression level of an indicator polynucleotide is 1481 and the average expression level from the experiment is 1208, then k is $1/1208$ resulting in a corrected expected expression level of 1.23 (e.g., ($1/1208$) *1481).

The optimization technique can also correct for 3' bias, which occurs in some methods of RNA amplification, such as T7 amplification. In one embodiment, the optimization technique calculates the corrected expression level according to the following equation:

$$M_{i,j} = f(H_{i,b}) \quad (17)$$

where f is a function such as a linear or nonlinear equation and $H_{i,b}$ is the expected expression level for an indicator polynucleotide i which identifies a target polynucleotide located b bases from the 3' end of the RNA transcript in column j. For example, if the expression level for polynucleotides drops off linearly measured by the number of bases from the 3' end of the RNA transcript, function f can be represented by the following equation:

$$f(H_{i,b}) = k_1 - k_2 b \quad (18)$$

where $k_1$ is the maximum value at the 3' end of the polynucleotide and $k_2$ is the rate at which the expression level drops for each nucleotide base from the 3' end.

If $k_1$ is 1.00, $k_2$ is 1.2E-2, and the target polynucleotide is located 1,303 bases from the 3' end of the RNA transcript, then the value of function f is represented by the following equation:

$$M_{i,j} = f(H_{i,\,1303}) = 1.00 - 1.2E\text{-}4*1303 = 0.84364$$

Alternatively, the optimization technique can apply the 3' bias correction to the empirically derived expression levels of matrix H, rather than matrix M, resulting in the following equation:

$$H'_{1,1} = H_{i,j} f(H_{i,b})^{-1} = 11,869*(0.84364)^{-1} = 14,069$$

The optimization technique can use more complex functions when the expression level varies nonlinearly with respect to the distance from the 3' end. For example, the expression level might drop precipitously when b exceeds some value. The optimization technique can use a nonlinear equation to represent such a drop.

The optimization technique can apply multiple corrections to the same matrix as indicated by the following equation:

$$M'_{i,j}=(M_{i,j}*C^1_{i,j}*C^2_{i,j}* \ldots * C^n_{i,j} \qquad (19)$$

where M' is the corrected matrix, $M_{i,j}$ is a starting matrix element value, and the various $C_{i,j}$ are element-by-element multiplicative corrections such as the 3' bias correction described above. The optimization technique can represent the correction more generally by the following equation:

$$M'_{i,j}=f(M_{i,j}, C^1_{i,j}, C^2_{i,j}, \ldots, C^n_{i,j}) \qquad (20)$$

where the $C_{i,j}$s are correction factors that may be applied using element-by-element corrections, such as multiplication, addition, or subtraction. The optimization technique can alternatively apply the multiple correction factors to matrix H, rather than matrix M according to the following equations:

$$H'_{i,j}=H_{i,j}*(C^1_{i,j})^{-1}*(C^2_{i,j})^{-1}* \ldots *(C^n_{i,j})^{-1} \qquad (21)$$

$$H'_{i,j}=f(H_{i,j}, C^1_{i,j}, C^2_{i,j}, \ldots, C^n_{i,j}) \qquad (22)$$

where f is a function that applies each individual correction to the empirically derived expression level.

Correcting for Presence of Homologous Polynucleotides

In one embodiment, the optimization technique corrects for the presence of homologous polynucleotides in a sample. In particular, an indicator polynucleotide identifies a target polynucleotide in an RNA transcript, but it may also identify, albeit less strongly, a homologue of the target polynucleotide in a different RNA transcript. The RNA transcripts may differ by only a few bases. The optimization technique can correct for a homologue in the sample by adding a column to matrix M for the homologue. The column might have a value only in row i if no other indicator polynucleotide in the experiment identifies a subsequence of the different RNA transcript. The solution can be found in various ways, such as using a system of linear equations or a least squares algorithm as described above.

Figure 3:
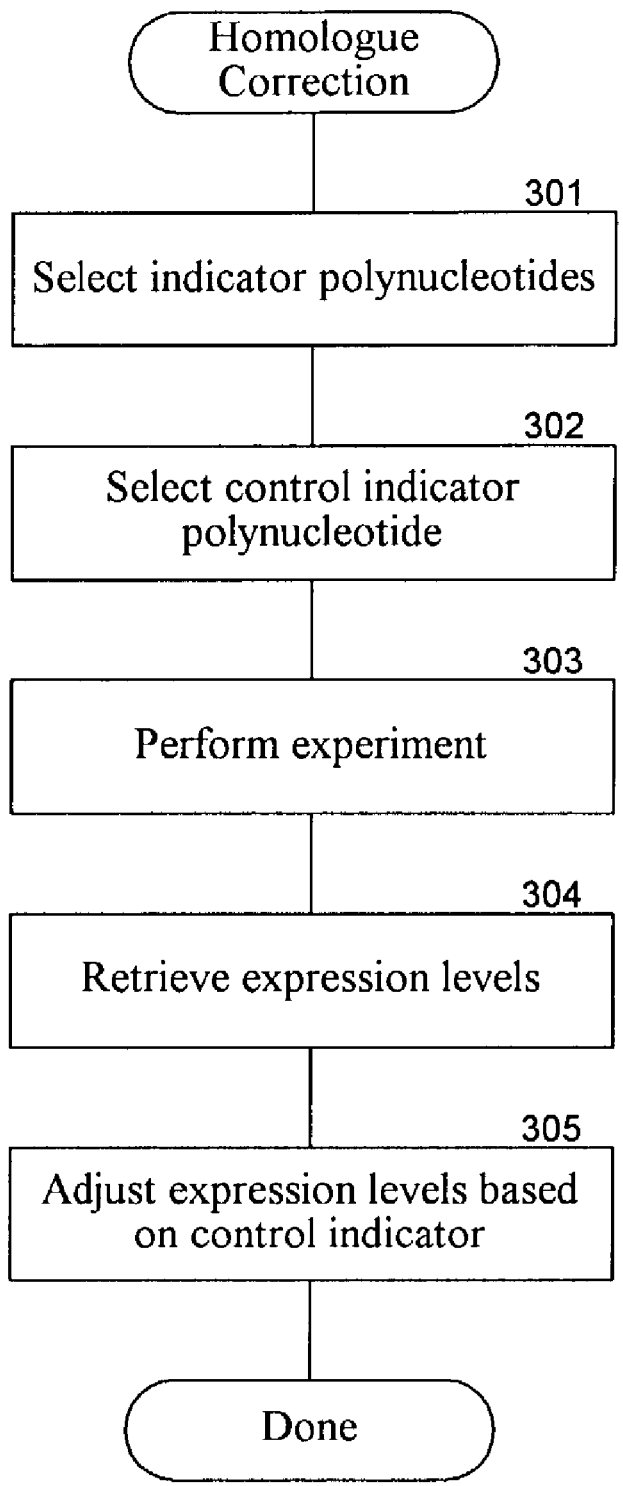
FIG. 3 is a flow diagram illustrating the overall process of correcting for hybridization of an indicator polynucleotide with a homologue of the target polynucleotide in one embodiment.

Alternatively, the optimization technique may determine the contribution to the expression level of the indicator polynucleotide resulting from the homologue if the expression level of the homologue by itself is known. Such determination would not have to rely on a single indicator polynucleotide to identify the expression level of both the target polynucleotide and the homologue. The optimization technique can determine the expression level of the homologue by selecting one or more "control indicator polynucleotides" specific to the homologue. FIG. 3 is a flow diagram illustrating the overall process of correcting for hybridization of an indicator polynucleotide with a homologue of the target polynucleotide in one embodiment. In block 301, the technique selects the indicator polynucleotide. In block 302, the technique selects a control polynucleotide. In block 303, the technique performs the experiment using the indicator polynucleotide and a control indicator polynucleotide. In block 304, the technique retrieves the expression levels from the experiment. In block 305, the technique adjusts the expression levels based on the characteristics of the control indicator polynucleotide. The optimization techniques can identify control indicator polynucleotides by selecting a region of the 3' untranslated of the homologue, confirming that it has no homologues by performing a similarity search (such as a BLAST search) against a database of known sequences, and designing control indicator polynucleotide to identify that region.

The optimization technique includes this control indicator polynucleotide in the experiment to correct the original indicator polynucleotide that may be weakly identifying the homologue instead of or in addition to the target polynucleotide. The correction may be performed according to the following equation:

$$H(P_i)=H(N_i)+kH(N'_i) \qquad (23)$$

where $H(P_i)$ is the expression level of indicator polynucleotide $P_i$, $H(N_i)$ is the detected expression level of the target polynucleotide $N_i$, k is a constant, and $H(N'_i)$ is the detected expression level of the homologous polynucleotide $N'_i$. The constant k accounts for differences between the target polynucleotide and its homologue. In such a case, the contribution of the homologous polynucleotide to the expression level measured for an indicator polynucleotide $P_i$ will be less than its independent expression level as measured by the control indicator polynucleotide. For example, if it is expected that the homologue will bind at ⅔ the proportion of its actual expression level, the value of k would be ⅔. The value of k may be determined empirically by performing hybridizations with the homologous polynucleotide and the indicator polynucleotide whose expression level is the numerator of k and with the homologous polynucleotide and the control indicator polynucleotide whose expression level is the denominator of k. Alternatively it may be calculated theoretically using an equation such as the following equation:

$$H(P_i|N'_i)=f(P_i, N'_i) \qquad (24)$$

where $H(P_i|N'_i)$ is the empirically derived expression level of polynucleotide $P_i$ when hybridized to a sample containing polynucleotide $N'_i$, and $f(P_i, N'_i)$ is a function of the two polynucleotides that are binding. The function f may take into consideration various factors such as the number of matches, the individual melting temperatures of the polynucleotides assuming perfect matches, base stacking, salt concentration, GC content, the precise pairing of mismatched bases, number of hydrogen bonds, magnesium concentration, primer concentration, length of perfectly matching regions, melting temperature of perfectly matching regions, distance of mismatches from the ends of the polynucleotides, and so on.

In the following example, the optimization technique corrects for an indicator polynucleotide that identifies a target polynucleotide and its homologue. The control indicator polynucleotide is used to determine the independent expression level of the RNA containing the homologue. The optimization technique calculates the value of the constant k as 0.723. When the experiment is run with the indicator polynucleotide and the control indicator polynucleotide, the resulting expression levels are 36,366 and 15,695, respectively. The optimization technique calculates the independent expression level of the target polynucleotide as follows:

$$36366=H(N_i)+0.723*15695$$

$$H(N_i)=36366-0.723*15695=25018$$

Alternatively, the optimization technique can apply the homologue correction as a correction matrix to matrix H, rather than matrix M.

The present invention may be practiced using one or more arrays, in which one or more indicator molecules are spotted onto an activated slide, such as produced by Motorola or other suppliers. Alternatively, the indicator molecules are synthesized directly on the slide, as with Agilent's array technology. The indicator molecules may also be used in a PCR-based array. Following synthesis or spotting, an expression experiment is conducted, e.g., using a tissue sample (with mRNA possibly extracted using random hexamers or another random sampling technique to correct for 3' bias), and the presence of a hybridization product is detected and, typically, quantified to obtain a measure of relative expression.

From the foregoing, it will be appreciated that specific embodiments of the invention have been described herein for purposes of illustration, but that various modifications may be made without deviating from the spirit and scope of the invention. For example, one skilled in the art will recognize the various ways in which the temperature balancing method and other indicator polynucleotide selection, optimization and correction techniques described here can be combined with existing methods. For example, the indicator polynucleotide selection techniques may be implemented or executed by means of a computer. Accordingly, the invention is not limited except as by the appended claims.

We claim:

1. A method for constructing a nucleotide array comprising a plurality of exon-exon junction indicator polynucleotides for detecting splice variants of a gene, comprising:

identifying a plurality of indicator polynucleotides for exon-exon junctions of splice variants of the gene, wherein each indicator polynucleotide, in the plurality, hybridizes to an exon-exon junction and has a melting temperature, and comprises a first portion that hybridizes to a 5' exon of the exon-exon junction and a second portion that hybridizes to a 3' exon of the exon-exon junction, each portion having a length and a melting temperature;

adjusting the length of at least one of the portions of at least one of the identified indicator polynucleotides so that the melting temperatures of the first portion and the second portion of each indicator polynucleotide are approximately balanced, and the melting temperatures of the identified indicator polynucleotides are optimized to minimize the overall differences in melting temperature; and constructing an array comprising the identified plurality of indicator polynucleotides.

* * * * *